(12) United States Patent
Toda et al.

(10) Patent No.: US 8,728,771 B2
(45) Date of Patent: May 20, 2014

(54) L-SUCCINYLAMINOACYLASE AND PROCESS FOR PRODUCING L-AMINO ACID USING IT

(75) Inventors: Atsushi Toda, Tsuruga (JP); Sachio Iwai, Tsuruga (JP); Yoshiaki Nishiya, Tsuruga (JP); Shinya Kumagai, Hachimantai (JP)

(73) Assignees: Toyo Boseki Kabushiki Kaisha, Osaka-shi (JP); Sekisui Medical Co., Ltd., Tokyo (JP)

( * ) Notice: Subject to any disclaimer, the term of this patent is extended or adjusted under 35 U.S.C. 154(b) by 149 days.

(21) Appl. No.: 13/139,205

(22) PCT Filed: Dec. 10, 2009

(86) PCT No.: PCT/JP2009/006770
§ 371 (c)(1),
(2), (4) Date: Jun. 10, 2011

(87) PCT Pub. No.: WO2010/067613
PCT Pub. Date: Jun. 17, 2010

(65) Prior Publication Data
US 2011/0250653 A1  Oct. 13, 2011

(30) Foreign Application Priority Data
Dec. 11, 2008  (JP) .................................. 2008-315233

(51) Int. Cl.
*C12P 13/04* (2006.01)
*C12N 9/80* (2006.01)
*C12N 15/00* (2006.01)

(52) U.S. Cl.
USPC .......................... 435/106; 435/228; 435/320.1

(58) Field of Classification Search
None
See application file for complete search history.

(56) References Cited

FOREIGN PATENT DOCUMENTS

| JP | 62-44181 A | * | 2/1987 |
|---|---|---|---|
| JP | 5-328972 A | | 12/1993 |
| JP | 2006-055131 A | | 3/2006 |
| JP | 2006-067870 A | | 3/2006 |
| JP | 2008-061642 A | | 3/2008 |
| JP | 2008-307006 A | | 12/2008 |
| WO | 2009/136500 A1 | | 11/2009 |

OTHER PUBLICATIONS

UniProt Accession No. B4B154, Sep. 2008, 1 page.*
Definition of "represent", obtained from Merriam-Webster online dictionary at www.merriam-webster.com, last viewed on Nov. 14, 2011.*
Amersham Protein Purification Handbook, Oct. 2001, p. 59.*
English-language translation of JP 62-44181, Nov. 2011, 15 pages.*
Feng, L., et al. "Amidohydrolase [*Geobacillus thermodenitrificans* NG80-2].", NCBI Sequence Revision History [online]; Accession: 001124936, <http://www.nchi.nlm.nih.gov/sviewer/viewer.fcgi?138894483:NCBI:23439857> Jul. 29, 2008 uploaded, [retrieved on Feb. 23, 2010], cited in ISR.
Lucas S., et al., "*Geobacillus* sp. G11MC16 ctg12, whole genome shotgun sequence.", NCBI Sequence Revision History [online]; Accession : NZ_ABVH 0100001, <http://www.ncbi.nlm.nih.gov/sviewer/viewer.fcgi?196247544: WGS:28954631>,Aug. 15, 2008 uploaded, [retrieved on Feb. 23, 2010], cited in ISR.
Sakai A. et al., "Evolution of enzymatic activities in the enolase superfamily: N-sucinylamino acid racemase and a new pathway for the irreversible conversion of D- to L-amino acids.", Biochemistry, 2006, 45(14), 4455-62, cited in ISR.
"Amidohydrolase [*Geobacillus* sp. G11MC16].", NCBI Sequence Revision History[online]; Accession:ZP_03146617, <http://www.ncbi.nlm.nih.gov/sviewer/viewer.fcgi?196247915:WGS:28954631>, Aug. 15, 2008 uploaded, [retrieved on Oct. 19, 2010], cited in ISR.
Nazina T. N., et al., "Taxonomic study of aerobic thermophilic bacilli: descriptions of *Geobacillus subterraneus* gen. nov., sp. nov. and *Geobacillus uzenensis* sp. nov. from petroleum reservoirs and transfer of *Bacillus stearothermophilus, Bacillus thermocatenulatus, Bacillus thermoleovorans, Bacillus kaustophilus, Bacillus thermoglucosidasius* and *Bacillus thermodenitrificans* to *Geobacillus* as the new combinati ons *G. stearothermophilus, G. thermocatenulatus, G. thermoleovorans, G. kaustophilus, G. thermoglucosidasius* and *G. thermodenitrificans*." Int. J. Sys. Evol. Microbiol. 51:433-446, 2001.
Cho, Hong-Yon et al. "Thermostable Dipeptidase from *Bacillus stearothermophilus*: Its Purification, Characterization, and Comparison with Aminoacylase," J. Biochem, Received for publication Sep. 1, 1987, vol. 103 No. 4, pp. 622-628, cited in ISR.
International Search Report of PCT/JP2009/006770, date of mailing Mar. 9, 2010.
Takami, H. et al "Accession: Q5L1H1, Definition: Amidohyrolase," NCBI sequence Revision History, Oct. 31, 2006.
Feng, L. et al "Accession: YP_001124936, Definition: Amidohydrolase [*Geobacillus thermodenitrificans* NG80-2],", NCBI sequence Revision History, Dec. 12, 2007.
Batisse, N. et al "Two Amino Acid Amidohydrolase Genes Encoding L-Stereospecific Cabamoylase and Aminoacylase Are Organized in a Common Operon in *Bacillus stearothermophilus*," Applied and Environmental Microbiology, Feb. 1997, vol. 63 No. 2, pp. 763-766.
Feng, Lu et al "Genome and proteome of long-chain alkane degrading *Geobacillus thermodentrificans* NG80-2 isolated from a deep-subsurface oil reservoir," Proceedings of the National Academy of Sciences USA, Mar. 27, 2007, pp. 5602-5607.
International Search Report of PCT/JP2009/002006, mailing date Aug. 18, 2009.
Kumagai, Shinya et al "Defluvibacter sp. A131-3-kabu ga Sansei suru Shinki D-aminoacylase no Seisei to Shoseishitsu," Japan Society for Bioscience, Biotechnology, and Agrochemistry 2004 Nendo Taikai Koen Yoshishu, Mar. 5, 2004, p. 119 2B04p19.
Notification of Transmittal of Translation of the International Preliminary Report on Patentability (Form PCT/IB/338 of International Application No. PCT/JP2009002006 mailed Dec. 13, 2010 with Forms PCT/IB/373 and PCT/ISA/237.
Ngo et al. in The Protein Folding and Tertiary Structure Prediction, 1994, Merz et al. (ed.), Birkhauser, Boston, MA, pp. 433 and 492-495.

* cited by examiner

*Primary Examiner* — David J Steadman
(74) *Attorney, Agent, or Firm* — Westerman, Hattori, Daniels & Adrian, LLP (57) ABSTRACT

The present invention provides a L-succinylacylase consisting of: (a) a protein coded by a gene consisting of a nucleic acid sequence shown in SEQ ID No: 1; (b) a protein consisting of an amino acid sequence shown in SEQ ID No: 2; (c) a protein coded by a polynucleotide which hybridizes under a stringent condition with a nucleic acid sequence which is complementary to the nucleic acid sequence shown in SEQ ID No: 1 and having an L-succinylaminoacylase activity; or (d) a protein which consists of an amino acid sequence where one or several amino acid(s) is/are substituted, deleted, inserted and/or added in the protein consisting of the amino acid sequence shown in SEQ ID No: 2 and has an L-succinylaminoacylase activity. This enzyme is able to produce a sterically bulky unnatural amino acid such as L-tert-leucine etc. which is useful as an intermediate for pharmaceuticals.

9 Claims, 2 Drawing Sheets

L-SUCCINYLAMINOACYLASE AND PROCESS FOR PRODUCING L-AMINO ACID USING IT

TECHNICAL FIELD OF THE INVENTION

The present invention relates to a novel L-succinylaminoacylase originated from thermophilic bacteria and, more particularly, it relates to a novel L-succinylaminoacylase which is able to efficiently utilize, as a substrate, a sterically bulky unnatural amino acid such as N-succinyl-L-tert-leucine, N-succinyl-L-biphenylalanine, N-succinyl-L-cyclohexylglycine, N-succinyl-L-dichlorophenylalanine or N-succinyl-L-bromophenylalanine. It also relates to a process for producing an L-amino acid using this enzyme.

BACKGROUND ART

L-amino acids are useful in many industrial fields such as pharmaceuticals, agricultural chemicals and foods. With regard to the industrially useful L-amino acid for example, there have been known L-lysine, L-threonine, L-isoleucine and L-proline used as additives for animal feeds, ingredients for health foods, amino acid transfusion, etc.; L-arginine and L-ornithine used as ingredients for hepatic function promoters, amino acid transfusion and multi-amino acid preparations; L-histidine used as hepatic function promoters and precursor for histamine; L-phenylalanine used as a precursor for sweeteners; and L-tert-leucine, L-biphenylalanine, L-cyclohexylglycine, L-dichlorophenylalanine and L-bromophenylalanine etc. used as intermediates for various pharmaceuticals. Accordingly, there has been a demand for an efficient production of those useful L-amino acids in a state of being separated from D-amino acids.

As to a process for producing the L-amino acid, there has been a conventional method where a racemic N-acylamino acid is synthesized and then only an L-form compound in the racemic modification is hydrolyzed using an enzyme called an L-aminoacylase. In result, only L-amino acid is specifically produced. As to the L-aminoacylase used for that method, there have been known, for example, an L-aminoacylase originated from *Penicillium funiculosum* (Patent Document 1) and an L-aminoacylase originated from *Streptomyces mobaraensis* (Patent Document 2).

L-aminoacylases disclosed in Patent Documents 1 and 2 are excellent in a hydrolyzing ability. Their substrate specificity is, however, still unsatisfactory whereby they are unable to recognize, as a substrate, a sterically bulky unnatural amino acid such as N-acyl-L-tert-leucine, N-acyl-L-biphenylalanine, N-acyl-L-cyclohexylglycine, N-acyl-L-dichlorophenylalanine or N-acyl-L-bromophenylalanine etc. Therefore, according to the method using L-aminoacylase disclosed in Patent Documents 1 and 2, it has been impossible to optically resolve a sterically bulky unnatural amino acid such as N-acyl-DL-tert-leucine etc. and it has been impossible to produce a sterically bulky unnatural amino acid such as L-tert-leucine which is a useful intermediate for pharmaceuticals.

The present inventors have recently found that the L-succinylaminoacylase obtained from NCA 1503 strain of *Geobacillus stearothermophilus* which is a kind of thermophilic bacteria is able to recognize N-succinyl-L-tert-leucine as a substrate, determined a nucleic acid sequence of the gene coding for this L-succinylaminoacylase and filed a patent application (Patent Document 3). The L-succinylaminoacylase disclosed in Patent Document 3 is able to utilize N-succinyl-L-tert-leucine as a substrate, and thus it has the substrate specificity which has not been achieved in the conventional L-aminoacylases. However, it still has a problem in terms of its enzymatic activity. Further, with regard to the substrate specificity to sterically bulky unnatural amino acids other than N-succinyl-L-tert-leucine, it is merely confirmed in Patent Document 3 that this L-succinylaminoacylase is able to utilize N-succinyl-L-cyclohexylglycine and N-succinyl-L-4-bromophenylalanine as a substrate.

PRIOR ART DOCUMENTS

Patent Documents

Patent Document 1: Japanese Patent Application Laid-Open (JP-A) No. 328972/93
Patent Document 2: Japanese Patent Application Laid-Open (JP-A) No. 2006-67870
Patent Document 3: WO 2009/136500

DISCLOSURE OF THE INVENTION

Problem that the Invention is to Solve

The present invention has been created in a point of view of the problems of the prior art as such and an object thereof is to provide a novel L-aminoacylase which is able to produce a sterically bulky unnatural amino acid such as L-tert-leucine, L-biphenylalanine, L-cyclohexylglycine, L-dichlorophenylalanine or L-bromophenylalanine, which are useful as intermediates for pharmaceuticals.

Means for Solving the Problem

In order to achieve the above-mentioned object, the present inventors have investigated the enzymatic activity of L-succinylaminoacylases originated from various organisms and, as a result, they have found that the L-succinylaminoacylase obtained from the IFO 12983 strain of *Geobacillus stearothermophilus* is able to efficiently utilize N-succinyl-L-tert-leucine as a substrate as compared with the L-succinylaminoacylase disclosed in Patent Document 3. They have also found that the L-succinylaminoacylase obtained from this strain is able to efficiently utilize, as a substrate, not only N-succinyl-L-tert-leucine but also other sterically bulky unnatural amino acids such as N-succinyl-L-biphenylalanine, N-succinyl-L-cyclohexylglycine, N-succinyl-L-dichlorophenylalanine or N-succinyl-L-bromophenylalanine. The present inventors have then determined the nucleic acid sequence of the gene which codes for this L-succinylaminoacylase whereupon the present invention has been accomplished.

Thus, in accordance with the present invention, there is provided a protein which is characterized in being represented by any of the following (a) to (d).
(a) a protein coded by a gene consisting of a nucleic acid sequence shown in SEQ ID No: 1;
(b) a protein consisting of an amino acid sequence shown in SEQ ID No: 2;
(c) a protein coded by a polynucleotide which hybridizes under a stringent condition with a nucleic acid sequence which is complementary to the nucleic acid sequence shown in SEQ ID No: 1 and having an L-succinylaminoacylase activity; and
(d) a protein which consists of an amino acid sequence where one or several amino acid(s) is/are substituted, deleted, inserted and/or added in the protein consisting of the amino acid sequence shown in SEQ ID No: 2 and has an L-succinylaminoacylase activity.

In accordance with the present invention, there is further provided a gene which is characterized in being represented by any of the following (a) to (d).

(a) a gene which consists of the nucleic acid sequence shown in SEQ ID No: 1;
(b) a gene which codes for the protein consisting of the amino acid sequence shown in SEQ ID No: 2;
(c) a gene which hybridizes under a stringent condition with the nucleic acid sequence which is complementary to the nucleic acid sequence shown in SEQ ID No: 1 and codes for a protein having an L-succinylaminoacylase activity; and
(d) a gene which consists of a nucleic acid sequence corresponding to an amino acid sequence where one or several amino acid(s) is/are substituted, deleted, inserted and/or added in the protein consisting of the amino acid sequence shown in SEQ ID No: 2 and codes for a protein having an L-succinylaminoacylase activity.

In accordance with the present invention, there is furthermore provided a process for producing the above protein which is characterized in comprising steps of: inserting the above gene into a vector to prepare a recombinant vector; transforming a host cell using said recombinant vector to prepare a transformant; and culturing this transformant.

In accordance with the present invention, there is still further provided a process for producing an L-amino acid which is characterized in comprising a step of specifically hydrolyzing N-succinyl-L-amino acid in N-succinyl-DL-amino acid using the above-mentioned protein.

Advantages of the Invention

Unlike the L-aminoacylase which has been known conventionally, the L-succinylaminoacylase of the present invention is able to efficiently utilize, as a substrate, a sterically bulky unnatural amino acid such as N-succinyl-L-tert-leucine, N-succinyl-L-biphenylalanine, N-succinyl-L-cyclohexylglycine, N-succinyl-L-dichlorophenylalanine or N-succinyl-L-bromophenylalanine whereby it is able to efficiently produce L-tert-leucine, L-biphenylalanine, L-cyclohexylglycine, L-dichlorophenylalanine or L-bromophenylalanine, which are useful as intermediates for pharmaceuticals.

BEST MODE FOR CARRYING OUT THE INVENTION

The L-succinylaminoacylase of the present invention is either (a) a protein coded by a gene consisting of a nucleic acid sequence shown in SEQ ID No: 1 or (b) a protein consisting of an amino acid sequence shown in SEQ ID No: 2. SEQ ID No: 1 is a nucleic acid sequence of L-succinylaminoacylase of IF012983 strain of *Geobacillus stearothermophilus* which is a kind of thermophilic bacteria while SEQ ID No: 2 is an amino acid sequence thereof.

The proteins of the above (a) and (b) have a characteristic that they are able to specifically hydrolyze only L-form compound of N-succinyl-L-amino acid among racemic N-succinylamino acid whereby L-amino acid is specifically produced. Although both N-acetylamino acid and N-succinylamino acid are considered to be present normally in organisms, the above proteins (a) and (b) have at least 100-fold higher activity to N-succinylamino acid than to N-acetylamino acid. From the above, it can be said that the above proteins (a) and (b) are the enzymes which catalyze the reaction of producing L-amino acid and succinic acid by a specific hydrolysis of N-succinyl-L-amino acid or, in other words, they are L-succinylaminoacylases.

The most noteworthy characteristic of the L-succinylaminoacylase of the present invention is that it is able to efficiently utilize a sterically bulky unnatural amino acid such as N-succinyl-L-tert-leucine, N-succinyl-L-biphenylalanine, N-succinyl-L-cyclohexylglycine, N-succinyl-L-dichlorophenylalanine or N-succinyl-L-bromophenylalanine. Among those sterically bulky unnatural amino acids, particularly with regard to N-succinyl-L-tert-leucine, N-succinyl-L-biphenylalanine, and N-succinyl-L-cyclohexylglycine, the L-succinylaminoacylase of the present invention is able to utilize those unnatural amino acids significantly efficiently, as shown in Example 7 which will be mentioned later, as compared with the L-succinylaminoacylase disclosed in Patent Document 3. The L-succinylaminoacylase of the present invention and that disclosed in Patent Document 3 are the enzymes originated from different strains of the same organism. It is quite surprising that the enzymes originated from near origins as such have greatly different enzymatic activities. This cannot be easily predicted by persons skilled in the art.

Physical and chemical properties of the L-succinylaminoacylase of the present invention are as shown in the following (i) to (v).

(i) Molecular weight: 43 kDa (SDS-PAGE);
(ii) Substrate specificity: It reacts to N-succinyl-tert-leucine, N-succinyl-biphenylalanine, N-succinylcyclohexylglycine, N-succinyl-dichlorophenylalanine, and N-succinyl-bromophenylalanine;
(iii) Temperature stability: When it is subjected to a heating treatment for 30 minutes, it is stable at 70° C. and is inactivated at 75° C. or higher;
(iv) Optimum temperature: When it is made to react at pH 7 to 8, its action is optimum at the temperature of 55 to 60° C.; and
(v) Optimum pH: When it is made to react at 60° C. for 30 minutes, its action is optimum at pH 7.

The L-succinylaminoacylase of the present invention exhibits its activity when divalent or univalent metal ion is made to react at the final concentration of 0.1 mM to 1 M therewith. Examples of the divalent or univalent metal ion include $Mn^{2+}$, $Co^{2+}$, $Mg^{2+}$, $Ca^{2+}$, $Ni^{2+}$ and $K^+$ and, among them, $Co^{2+}$ is particularly preferred. It has been known that, when $Co^{2+}$ is used, the activity increased to an extent of twice or more as compared with the case where $Zn^{2+}$ is used.

The present invention also covers (a) a gene consisting of the nucleic acid sequence shown in SEQ ID No: 1 and (b) a gene coding for the protein consisting of the amino acid sequence shown in SEQ ID No: 2. They are the genes corresponding to the proteins of the above (a) and (b).

The L-succinylaminoacylase of the present invention is not limited to the above (a) and (b), and covers (c) a protein coded by a polynucleotide which hybridizes under a stringent condition with a nucleic acid sequence which is complementary to the nucleic acid sequence shown in SEQ ID No: 1 and having an L-succinylaminoacylase activity or (d) a protein which consists of an amino acid sequence where one or several amino acid (s) is/are substituted, deleted, inserted and/or added in the protein consisting of the amino acid sequence shown in SEQ ID No: 2 and has an L-succinylaminoacylase activity. Also, the genes of the present invention covers (c) a gene which hybridizes under a stringent condition with the nucleic acid sequence which is complementary to the nucleic acid sequence shown in SEQ ID No: 1 and codes for a protein having an L-succinylaminoacylase activity or (d) a gene which consists of a nucleic acid sequence corresponding to an amino acid sequence where one or several amino acid (s) is/are substituted, deleted, inserted and/or added in the protein consisting of the amino acid sequence shown in SEQ ID No: 2 and codes for a protein having an L-succinylaminoacylase activity. That is because, even if the nucleic acid sequence of the gene coding for the protein is partially modified or even if the amino acid sequence of the protein is partially modified as a result thereof, it is often the case that they are functionally identical proteins. That is also because, when the gene of the L-succinylaminoacylase of the present invention is integrated into a host organism (such as *Escherichia coli*) other than the organism wherefrom the gene is originated to express the L-succinylaminoacylase of the present invention, it is often the case that the nucleic acid sequence of the L-succinylaminoacylase is modified in accordance with the codon usage of the above host organisms so that the expression efficiency of the L-succinylaminoacylase is enhanced.

The gene coding for the protein of the above (c) can be prepared by means of colony or plaque hybridization using a nucleic acid sequence being complementary to the nucleic acid sequence shown in SEQ ID No: 1 or a part thereof as a probe. The term. "stringent condition" used in this description stands for the condition where the so-called specific hybridization occurs and non-specific hybridization does not occur. For example, it may be such a condition where only such a DNA having a homology of 60% or more, preferably 80% or more, more preferably 90% or more, more preferably 95% or more, more preferably 97% or more, more preferably 98% or more, and more preferably 99% or more to a nucleic acid sequence is specifically hybridized.

A stringent condition can be created by adjusting the salt concentration, temperature, etc. of a hybridization solution. An example is that a pre-hybridization is carried at 42° C. for one night in a hybridization solution containing 25% of formamide (50% of formamide in the case of severer condition), 4×SSC, 50 mM of Hepes (pH 7), 10×Denhardt's solution and 20 µg/mL of modified salmon sperm DNA and, after that, a labeled probe is added thereto followed by keeping at 42° C. for one night to conduct the hybridization. The washing solution and the temperature condition during the washing conducted thereafter are at about "1×SSC, 0.1% SDS and 37° C.", and the severer condition is at about "0.5×SSC, 0.1% SDS and 42° C.", and the more severer condition is at about "0.2× SSC, 0.1% SDS and 65° C.". The above combinations of SSC and SDS with temperature condition are mere examples and persons skilled in the art can achieve the same stringency as above by appropriately combining the above or other factors (such as probe concentration, probe length or hybridization reaction time) determining the stringency of the hybridization.

The fact whether the gene obtained by the hybridization is a gene which codes for the protein having an L-succinylaminoacylase activity can be confirmed, for example, by such a means that the resulting gene is introduced into *Escherichia coli* to prepare a transformant, the transformant is cultured to produce an enzyme protein, the enzyme protein is purified and added to N-succinyl-DL-amino acid and production of an L-amino acid is measured by chromatography or the like.

Further, the gene of the protein of the above (d) (i.e. the gene which consists of a nucleic acid sequence corresponding to an amino acid sequence where one or several amino acid(s) is/are substituted, deleted, inserted and/or added in the protein consisting of the amino acid sequence shown in SEQ ID No: 2 and codes for a protein having an L-succinylaminoacylase activity) can be obtained, for example, by modifying the nucleic acid sequence shown in SEQ ID No: 1 utilizing a commercially available kit such as KOD-Plus-Mutagenesis Kit (manufactured by Toyobo) or a PCR method. The enzyme reactivity of the manipulated gene coding L-succinylaminoacylase can be confirmed by the same method described above.

Production of the L-succinylaminoacylase of the present invention can be easily carried out by such a manner that the gene thereof is inserted into an appropriate vector to prepare a recombinant vector, an appropriate host cell is transformed using said recombinant vector to prepare a transformant and the resulting transformant is cultured.

There is no particular limitation for the vector so far as it is capable of retaining replication ability or of autonomous replication in various host cells which are prokaryotic and/or eukaryotic cells and examples thereof include plasmid vector, phage vector and virus vector. Preparation of the recombinant vector may be carried out by a conventional method and it can be easily conducted, for example, in such a manner that the vector as such is ligated to the gene of L-succinylaminoacylase of the present invention using an appropriate restriction enzyme and ligase, if necessary, together with linker or adaptor DNA. In the case of gene fragment which is prepared by amplification using a DNA polymerase which adds one base to the amplified terminal such as Taq polymerase, connection to the vector by means of TA cloning is also possible.

As to the host cells, those which have been known conventionally can be used and, although there is no particular limitation provided that a recombination expression system therefor has been established, preferred examples include microbes such as *Escherichia coli, Bacillus subtilis*, actinomycete, *aspergillus* or yeast as well as insect cells, animal cells and higher plants, more preferred examples are microbes and the particular preferred example is *E. coli* (such as K12 strain or B strain). Preparation of the transformant may be carried out according to the conventional method.

When the resulting transformant is cultured for a predetermined period under the appropriate culturing condition for the host cells, L-succinylaminoacylase of the present invention is expressed from the integrated gene and is accumulated in the transformant.

Although the L-succinylaminoacylase of the present invention accumulated in the transformant may be used without purification, a purified one may be used as well. As to a method for the purification, the conventionally known one can be used and, for example, it can be conducted by such a manner that the transformant after the culture or a cultured product thereof is homogenized in an appropriate buffer, a cell extract is prepared therefrom by treating with ultrasonic wave or surfactant and separating means usually utilized for separation and purification of protein are appropriately combined. Examples of the separating means as such include a method where the difference in solubility is utilized such as salting out or solvent precipitation method; a method where the difference in molecular weight is utilized such as dialysis, ultrafiltration, gel filtration, unmodified polyacrylamide gel electrophoresis (PAGE) or sodium dodecylsulfate-polyacrylamide gel electrophoresis (SDS-PAGE); a method where the charge is utilized such as ion-exchange chromatography or hydroxyapatite chromatography; a method where the specific affinity is utilized such as affinity chromatography; a method where the difference in hydrophobicity is utilized such as reverse phase high-performance liquid chromatography; and a method where the difference in isoelectric point is utilized such as isoelectric electrophoresis, although the present invention is not limited to the above-mentioned ones.

Now a method for producing the L-amino acid using the L-succinylaminoacylase of the present invention will be illustrated. The L-amino acid according to the present invention is produced by a step of specifically hydrolyzing N-succinyl-L-amino acid (L-form compound) in the N-succinyl-DL-amino acid (racemic modification) using the L-succinylaminoacylase of the present invention.

To be more specific, this step can be carried out by such a manner that the L-succinylaminoacylase of the present invention and N-succinyl-DL-amino acid which is the starting material are dissolved in an appropriate solution and the resulting reaction solution is made to react under an appropriate condition.

Distilled water may be enough for the solution to be used and, if necessary, a buffer such as phosphate or Tris may be used as well. When a buffer is used, its concentration is preferred to be 20 to 200 mM and the pH is preferred to be 6.5 to 8.

The L-succinylaminoacylase of the present invention is used preferably in a concentration of 5 to 500 mg/L (100 to 10000 U/L) in the reaction solution. Further, since the L-succinylaminoacylase of the present invention retains its activity by addition of divalent or univalent metal ion in the final concentration of 0.1 mM to 1 M (preferably 0.1 to 1 mM) as mentioned already, it is necessary to add divalent or univalent metal ion to the reaction solution. Examples of the divalent or univalent metal ion include $Mn^{2+}$, $Co^{2+}$, $Mg^{2+}$, $Ca^{2+}$, $Ni^{2+}$ and $K^+$ and, among them, $Co^{2+}$ is particularly preferred.

The N-succinyl-DL-amino acid which is to be made to react with the L-succinylaminoacylase of the present invention can be synthesized by various known methods such as a method disclosed in Sakai A., et al., *Biochemistry*, 2006, 45(14), 4455 to 62. Type of the DL-amino acid used as a starting material may be appropriately selected depending upon the type of the L-amino acid to be produced and it may be the naturally existing 20 kinds of amino acids and derivatives thereof and the unnatural amino acid such as tert-leucine, cyclohexylglycine, bromophenylalanine, biphenylalanine or dichlorophenylalanine and derivatives thereof.

Although the concentration of the N-succinyl-DL-amino acid in the reaction solution is not particularly limited, it is usually 1% by weight to 30% by weight.

In the process for producing the L-amino acid of the present invention, although there is no particular limitation for the temperature at which the reaction solution is made to react so far as it is the temperature where the L-succinylaminoacylase of the present invention acts well, it is usually preferred to be 20 to 70° C., more preferred to be 30 to 60° C., and much more preferred to be 55 to 60° C. With regard to the pH upon the reaction, although there is no particular limitation so far as it is the pH where the L-succinylaminoacylase of the present invention acts well, it is usually preferred to be pH 4 to 10, and more preferred to be pH 6 to 9. Although the reaction time is not particularly limited, it is usually about from one to seven day(s). The reaction time may be appropriately selected experimentally by taking into consideration the type of the L-amino acid to be produced, the desired producing amount and yield, amounts of the enzyme and the substrate used and the ratio thereof, reaction temperature, reaction pH, etc.

It is preferred that the process for producing the L-amino acid of the present invention further includes a step of racemizing N-succinyl-D-amino acid using N-succinylamino acid racemase to produce N-succinyl-L-amino acid. Since the L-succinylaminoacylase of the present invention specifically hydrolyzes only N-succinyl-L-amino acid in N-succinyl-DL-amino acid (racemic modification), another half of the racemic modification, which is N-succinyl-D-amino acid would be wasted. Accordingly, producing N-succinyl-L-amino acid by racemizing N-succinyl-D-amino acid with N-succinylamino acid racemase enables all the remaining N-succinyl-D-amino acid to be converted into L-amino acid.

N-succinylamino acid racemase is an enzyme which catalyzes both of a reaction which converts an L-form compound of N-succinylamino acid to a D-form compound and a reaction which converts a D-form compound to an L-form compound and makes their ratio almost equal (racemization). There is no particular limitation for the N-succinylamino acid racemase used in the production process of the present invention so far as it is able to racemize the N-succinylamino acid and the conventionally known ones such as N-acylamino acid racemase disclosed in Japanese Patent Application Laid-Open (JP-A) No. 2007-82534 and N-acylamino acid racemase disclosed in Japanese Patent Application Laid-Open (JP-A) No. 2008-61642 may be used.

The racemization reaction of the N-succinyl-D-amino acid using the N-succinylamino acid racemase is carried out, for example, by mixing a reaction solution containing N-succinyl-D-amino acid, N-succinylamino acid racemase and buffer under the following condition. Although there is no particular limitation for the reaction temperature so far as it is the temperature where the used N-succinylamino acid racemase acts well, it is usually preferred to be 25 to 70° C., and more preferred to be 37 to 70° C. Although there is no particular limitation for the pH upon the reaction so far as it is the pH where the N-succinylamino acid racemase acts well, it is usually preferred to be pH 5 to 9, and more preferred to be pH 6.5 to 8. The N-succinylamino acid racemase is used preferably in a concentration of 5 to 500 mg/L (500 to 50000 U/L) in the reaction solution. The N-succinylamino acid racemase retains its activity by addition of divalent metal ion in the final concentration of 0.1 mM to 1 M (preferably 0.1 to 1 mM). Examples of the divalent metal ion include $Mn^{2+}$, $Co^{2+}$, $Mg^{2+}$, $Fe^{2+}$ and $Ni^{2+}$ and, among them, $Co^{2+}$ is particularly preferred. When $Co^{2+}$ is made to react at the final concentration of 0.1 mM to 1 M, it exhibits the activity of twice or more higher in terms of relative activity as compared with the case where $Mn^{2+}$ is made to react at the final concentration of 0.1 mM to 1 M. As to the buffer used for the reaction of the N-succinylamino acid racemase, the same buffers as those used for the reaction of the L-succinylaminoacylase may be used. In the meanwhile, the N-acylamino acid racemase disclosed in Japanese Patent Application Laid-Open (JP-A) No. 2007-82534 has been found to be an N-succinylamino acid racemase which utilizes N-succinylamino acid as a more preferred substrate, as a result of the studies thereafter. Accordingly, the N-acylamino acid racemase disclosed in Japanese Patent Application Laid-Open (JP-A) No. 2007-

82534 may be used in combination with the L-succinylaminoacylase of the present invention.

Although the above-mentioned racemization reaction by the N-succinylamino acid racemase and hydrolyzing reaction by the L-succinylaminoacylase may be carried out separately, they are preferred to be conducted simultaneously. When they are simultaneously conducted, the microscopic analysis thereof is that, firstly, an L-form compound in the N-succinyl-DL-amino acid is deacylated (hydrolyzed) by the L-succinylaminoacylase of the present invention to give the aimed L-amino acid. Since the racemic state no longer exists when the L-form compound of the substrate is consumed, the N-succinylamino acid racemase further promotes the converting reaction of the D-form compound to the L-form compound. The N-succinyl-L-amino acid produced by the N-succinylamino acid racemase is successively converted to the L-amino acid by the L-succinylaminoacylase of the present invention. As a result of the repetition thereof, it is possible to convert nearly all of the N-succinyl-DL-amino acid to the L-amino acid theoretically. As to the reaction condition when racemization reaction and hydrolysis reaction are conducted simultaneously, although there is no particular limitation so far as it is within a range where the N-succinylamino acid racemase and the L-succinylaminoacylase of the present invention achieve the activity, it is preferred to conduct the reaction under the condition where the substrate concentration is 1% by weight to 30% by weight, the pH is 6 to 8 and the temperature is 30 to 60° C. As to the time needed for the racemization reaction and the hydrolyzing reaction, there is no particular limitation so far as it is such a time by which the N-succinyl-DL-amino acid used as the starting material is converted to the L-amino acid in a desired amount and, although it varies depending upon the charged amount, it is usually about one to seven day(s).

EXAMPLES

The present invention will now be specifically illustrated by way of the following Examples although the present invention is not limited to the following Examples.

Synthesis of N-succinyl-DL-amino Acid (1) Synthesis of N-succinyl-DL-tert-leucine An equimolar mixture of D-tert-Leucine (manufactured by Tokyo Kasei Kogyo) and L-tert-Leucine (manufactured by Tokyo Kasei Kogyo) (10 g) was dissolved in 50 mL of water and 15 g of 20% sodium hydroxide solution (manufactured by Nacalai tesque), then 8 g of succinic acid anhydride and 15 g of 20% sodium hydroxide solution (manufactured by Nacalai tesque) were added thereto and the mixture was made to react at 20 to 40° C. with stirring. After the reaction solution was neutralized with hydrochloric acid, it was extracted with ethyl acetate and then concentrated. The concentrate was dried with hexane followed by crystallizing to give 14 g of N-succinyl-DL-tert-leucine as white powder.

(2) Synthesis of N-succinyl-DL-valine

An equimolar mixture of D-valine (manufactured by Nacalai tesque) and L-valine (manufactured by Nacalai tesque) (10 g) was dissolved in 50 mL of water and 17 g of 20% sodium hydroxide solution (manufactured by Nacalai tesque), then 8.8 g of succinic acid anhydride (manufactured by Nacalai tesque) and 17 g of 20% sodium hydroxide solution (manufactured by Nacalai tesque) were added thereto and the mixture was made to react at 20 to 40° C. with stirring. After the reaction solution was neutralized with hydrochloric acid (manufactured by Nacalai tesque), it was extracted with ethyl acetate (manufactured by Nacalai tesque) and then concentrated. The concentrate was dried with hexane followed by crystallizing to give 15 g of N-succinyl-DL-valine as white powder.

(3) Synthesis of N-succinyl-DL-phenylalanine, N-succinyl-DL-tryptophan, N-succinyl-DL-asparagine, N-succinyl-DL-serine, N-succinyl-DL-tyrosine, N-succinyl-DL-cyclohexylglycine, N-succinyl-DL-4-bromophenylalanine, N-succinyl-DL-biphenylalanine, and N-succinyl-DL-3,4-dichlorophenylalanine Those N-succinyl-DL-amino acids were synthesized by the method according to the synthetic method for N-succinyl-DL-valine mentioned in (2).

Preparation of N-Succinylamino Acid Racemase (1) Preparation of N-Succinylamino Acid Racemase Disclosed in Japanese Patent Application Laid-Open (JP-A) No. 2008-61642

Chromosomal DNA of *Geobacillus stearothermophilus* NCA 1503 strain was purified by the following method. Thus, said strain in one platinum loop was inoculated to an LB liquid medium (a 30 mL test tube being chargeable with 5 mL; 1.0% of polypeptone, 0.5% of yeast extract and 1.0% of NaCl; pH 7.4) and subjected to a shake culture at 50° C. for one night. One mL of the cells was centrifuged (at 12,000 rpm for 10 minutes at 4° C.) to recover the cells. Chromosomal DNA was extracted from the recovered cells using MagExtractor-genome-kit (manufactured by Toyobo) in accordance with the procedure disclosed in the direction for use. About 20 µg of chromosomal DNA was prepared from 1 mL of the cells.

After that, N-succinylamino acid racemase gene (SEQ ID No: 3) originated from *Geobacillus stearothermophilus* NCA 1503 strain was amplified by means of PCR using the prepared chromosomal DNA as a template. As to the PCR primers, there were used a 5' primer (5'-AAG GAG GTA AAA TGG CGA TCA ACA TCG AGT AC-3' (SEQ ID No: 4)) and a 3' primer (5'-TCT AGA TTA TGC CGT CGC CGT ACG ATG AAA-3' (SEQ ID No: 5)). PCR was then conducted (for 30 cycles where each cycle comprised 94° C. for 15 seconds, 55° C. for 30 seconds and 68° C. for 90 seconds) using those PCR primers and KOD Plus DNA polymerase (manufactured by Toyobo) where the above-prepared chromosomal DNA as a template.

Then an operation was carried out using a cloning kit Target Clone-Plus (manufactured by Toyobo) according to the protocol therefor and the resulting gene was cloned to a vector pBluescript to give a recombinant expression plasmid pBSNAR1. Competent cells of *Escherichia coli* JM 109 strain (manufactured by Toyobo) was transformed using the pBSNAR1 to give a transformant. The resulting transformant was named *Escherichia coli* JM 109 (pBSNAR1).

A TB medium (500 mL) was placed in two 2-liter Sakaguchi's flasks, autoclaved at 121° C. for 20 minutes and allowed to cool and ampicillin and isopropyl-β-D-thiogalactoside which were separately subjected to aseptic filtration were added thereto so as to make their final concentrations 100 µg/mL and 0.1 mM respectively. To this medium was inoculated 5 mL of a culture solution of *Escherichia coli* JM 109 (pBSNAR1) cultured at 30° C. for 16 hours in LB medium containing ampicillin (100 µg/mL) followed by culturing at 37° C. for 24 hours with aeration and stirring. After finishing the culture, the cells were collected by centrifugal separation, suspended in 50 mM phosphate buffer (pH 7.5), crushed using a French press and centrifuged again and the supernatant liquid was obtained as a crude enzyme solution. The resulting crude enzyme solution was subjected to removal of nucleic acid using polyethyleneimine and to fractionation using ammonium sulfate, heated at 50° C. for 1 hour and dialyzed with 50 mM phosphate buffer (pH 7.5). Separation and purification were further conducted by column chromatography of DEAE Sepharose CL-6B (manufactured by GE Health Care Bioscience) and octyl-Sepharose (manufactured by GE Health Care Bioscience) each whereupon a pure enzyme specimen was prepared.

(2) Preparation of N-succinylamino Acid Racemase Disclosed in Japanese Patent Application Laid-Open (JP-A) No. 2007-82534

NdeI and BamHI sites were added to the upstream and the downstream areas, respectively of the gene (SEQ ID No: 6) of N-succinylamino acid racemase originated from *Chloroflexus aurantiacus* (hereinafter, it will be referred to as NAAAR), and the resulting recombinant gene was artificially synthesized according to a method disclosed in "Protocol of PCR Experiments for Plants" (Supplementary Issue of Saibo Kogaku) (pp. 84-89, published by Shujunsha). The resulting gene was cloned to a vector pBluescriptII KSN+ to give a recombinant expression plasmid pCFNAR. Competent cells of *Escherichia coli* DH5α strain (manufactured by Toyobo) was transformed using the pCFNAR to give a transformant. The resulting transformant was named *Escherichia coli* DH5α (pCFNAR).

A TB medium (500 mL) was placed in two 2-liter Sakaguchi's flasks, autoclaved at 121° C. for 20 minutes and allowed to cool and ampicillin and isopropyl-β-D-thiogalactoside which were separately subjected to aseptic filtration were added thereto so as to make their final concentrations 100 μg/mL and 0.1 mM respectively. To this medium was inoculated 5 mL of a culture solution of *Escherichia coli* DH5α (pCFNAR) cultured at 30° C. for 16 hours in LB medium containing ampicillin (100 μg/mL) followed by culturing at 37° C. for 24 hours with aeration and stirring. After finishing the culture, the cells were collected by centrifugal separation, suspended in 50 mM phosphate buffer (pH 7.5), crushed using a French press and centrifuged again and the supernatant liquid was obtained as a crude enzyme solution. The resulting crude enzyme solution was subjected to removal of nucleic acid using polyethyleneimine and to fractionation using ammonium sulfate, and dialyzed with 50 mM phosphate buffer (pH 7.5). Separation and purification were further conducted by column chromatography of DEAE Sepharose CL-6B (manufactured by GE Health Care Bioscience) whereupon a pure enzyme specimen was prepared.

Example 1

Preparation of L-succinylaminoacylase of the Present Invention

Chromosomal DNA of *Geobacillus stearothermophilus* IFO 12983 strain was purified by the following method. Thus, said strain in one platinum loop was inoculated to an LB liquid medium (a 30 mL test tube being chargeable with 5 mL; 1.0% of polypeptone, 0.5% of yeast extract and 1.0% of NaCl; pH 7.4) and subjected to a shake culture at 50° C. for one night. One mL of the cells was centrifuged (at 12,000 rpm for 10 minutes at 4° C.) to recover the cells. Chromosomal DNA was extracted from the recovered cells using MagExtractor-genome-kit (manufactured by Toyobo) in accordance with the procedure disclosed in the direction for use. About 20 μg of chromosomal DNA was prepared from 1 mL of the cells.

After that, L-succinylaminoacylase gene (SEQ ID No: 1) originated from *Geobacillus stearothermophilus* IFO 12983 strain was amplified by means of PCR using the prepared chromosomal DNA as a template. As to the PCR primers, there were used a 5' primer (5'-AAG GAG GTA AAA TGA AAG AAA TTA TTC AGC AGA TGA AAG C-3' (SEQ ID No: 7)) and a 3' primer (5'-TCT AGA TCA ATG ATT TGC AGC GAT AGA GAC ACG-3' (SEQ ID No: 8)). PCR was then conducted (for 30 cycles where each cycle comprised 94° C. for 15 seconds, 55° C. for 30 seconds and 68° C. for 90 seconds) using those PCR primers and KOD Plus DNA polymerase (manufactured by Toyobo) where the above-prepared chromosomal DNA as a template.

Then an operation was carried out using a cloning kit (Target Clone (Registered Trademark)-Plus, manufactured by Toyobo) according to the protocol therefor and the resulting vector was cloned to a vector pBluescript to give a recombinant expression plasmid pLSA2. Competent cells of *Escherichia coli* JM 109 strain (manufactured by Toyobo) was transformed using the pLSA2 to give a transformant. The resulting transformant was named *Escherichia coli* JM 109 (pLSA2).

A TB medium (500 mL) was placed in two 2-liter Sakaguchi's flasks, autoclaved at 121° C. for 20 minutes and allowed to cool and ampicillin and isopropyl-β-D-thiogalactoside which were separately subjected to aseptic filtration were added thereto so as to make their final concentrations 100 μg/mL and 0.1 mM respectively. To this medium was inoculated 5 mL of a culture solution of *Escherichia coli* JM 109 (pLSA2) cultured at 30° C. for 16 hours in LB medium containing ampicillin (100 μg/mL) followed by culturing at 37° C. for 24 hours with aeration and stirring. After finishing the culture, the cells were collected by centrifugal separation, suspended in 50 mM phosphate buffer (pH 7.5), crushed using a French press and centrifuged again and the supernatant liquid was obtained as a crude enzyme solution. The resulting crude enzyme solution was subjected to removal of nucleic acid using polyethyleneimine and to fractionation using ammonium sulfate, heated at 50° C. for 1 hour and dialyzed with 50 mM phosphate buffer (pH 7.5). Separation and purification were further conducted by column chromatography of DEAE Sepharose CL-6B (manufactured by GE Health Care Bioscience) and octyl-Sepharose (manufactured by GE Health Care Bioscience) each whereupon a pure enzyme specimen was prepared. The resulting specimen was confirmed to be a single substance as a result of SDS-PAGE.

Example 2

Synthesis of L-tert-leucine from N-succinyl-DL-tert-leucine Using the L-succinylaminoacylase of the Present Invention The N-succinyl-DL-tert-leucine synthesized in the above (1) was dissolved in distilled water and its pH was adjusted using 0.1N sodium hydroxide (manufactured by Nacalai tesque) to prepare a 5% by weight solution of N-succinyl-DL-tert-leucine (pH 7 to 8). To 10 ml of this solution were added 0.5 mM (final concentration) $CoCl_2$ and 0.5 ml of a 5.8 mg/ml solution of L-succinylaminoacylase prepared in Example 1 to give a reaction solution (pH 7 to 8). This reaction solution was kept at 57° C. for 144 hours with stirring. The sample was collected after 24 hours, 48 hours, 72 hours and 144 hours from the start of the reaction and subjected to an HPLC measurement under the following condition to confirm the peaks of succinyl-form compound and free-form compound whereby the synthesis of L-tert-leucine from N-succinyl-DL-tert-leucine was confirmed.

Column: Inertsil ODS-2 (particle size: 5 μm; 4.6 mm inner diameter×250 mm length) manufactured by GL Science Eluant: aqueous solution of phosphate (pH 2.3)/acetonitrile for HPLC=80:20

Flow rate: 0.8 mL/minute

Column temperature: 40° C.

Detection: 210 nm

Figure 1:
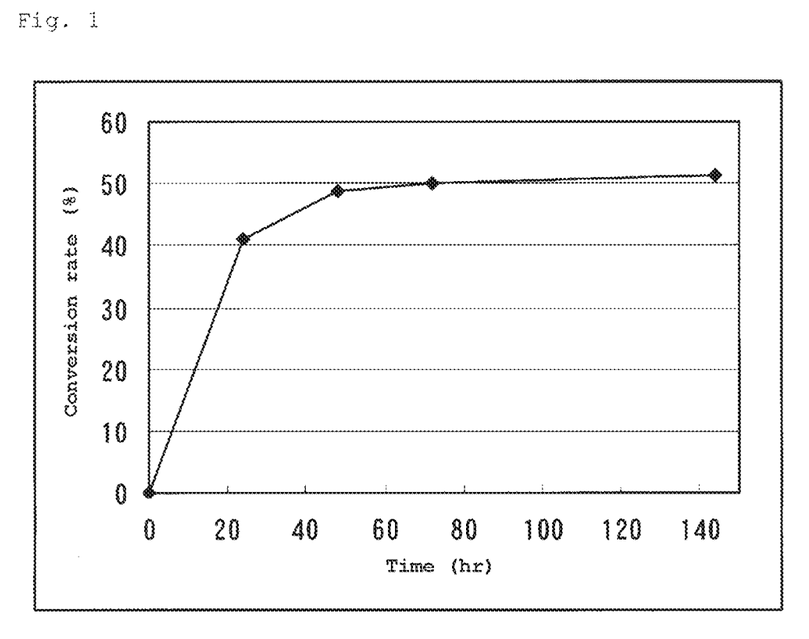
FIG. 1 shows the result of measurement of the yield of L-tert-leucine in Example 2 by means of HPLC. Time elapsed from the initiation of the reaction (hr) is shown in the abscissa while a conversion rate into L-tert-leucine (%) is shown in the ordinate.

Result of the HPLC measurement is shown in FIG. 1. As will be apparent from FIG. 1, the L-succinylaminoacylase of the present invention was able to synthesize L-tert-leucine from N-succinyl-DL-tert-leucine within a short period in a yield (hereinafter, it may be referred to as a "conversion rate") nearly equal to 50% which is the theoretically highest yield.

Example 3

Synthesis of each L-amino Acid Corresponding to N-succinyl-DL-valine, N-succinyl-DL-phenylalanine, N-succinyl-DL-tryptophan, N-succinyl-DL-asparagine, N-succinyl-DL-serine, N-succinyl-DL-tyrosine, and N-succinyl-DL-cyclohexylglycine Using the L-succinylaminoacylase of the Present Invention The reaction was carried out for 96 hours under the same condition as in Example 2 using N-succinyl-DL-valine, N-succinyl-DL-phenylalanine, N-succinyl-DL-tryptophan, N-succinyl-DL-asparagine, N-succinyl-DL-serine, N-succinyl-DL-tyrosine, or N-succinyl-DL-cyclohexylglycine synthesized in the above (2) and (3) instead of N-succinyl-DL-tert-leucine. However, concentration of each N-succinyl-DL-amino acid was made 10% by weight. After completion of the reaction, a sample was collected therefrom and subjected an HPLC measurement under the same condition as in Example 2 to calculate the conversion rate into each L-amino acid corresponding to N-succinyl-DL-valine, N-succinyl-DL-phenylalanine, N-succinyl-DL-tryptophan, N-succinyl-DL-asparagine, N-succinyl-DL-serine, N-succinyl-DL-tyrosine, and N-succinyl-DL-cyclohexylglycine.

The result is shown in Table 1. As will be apparent from Table 1, the L-succinylaminoacylase of the present invention was able to synthesize each of the corresponding L-amino acids from N-succinyl-DL-valine, N-succinyl-DL-phenylalanine, N-succinyl-DL-tryptophan, N-succinyl-DL-asparagine, N-succinyl-DL-serine, N-succinyl-DL-tyrosine, and N-succinyl-DL-cyclohexylglycine within a short period and efficiently. Particularly, the L-succinylaminoacylase of the present invention was able to synthesize L-cyclohexylglycine which is a unnatural amino acid in a yield being nearly equal to 50% which is the theoretically highest yield.

TABLE 1

| Substrate | Yield (%) |
|---|---|
| N-succinyl-DL-valine | 42.4 |
| N-succinyl-DL-phenylalanine | 37.5 |
| N-succinyl-DL-tryptophan | 31.4 |
| N-succinyl-DL-asparagine | 42.5 |
| N-succinyl-DL-serine | 43.4 |
| N-succinyl-DL-tyrosine | 19.1 |
| N-succinyl-DL-cyclohexylglycine | 49.2 |

Example 4

Synthesis of L-tert-leucine from N-succinyl-DL-tert-leucine Using the L-succinylaminoacylase of the Present Invention and N-Succinylamino Acid Racemase (i)

The reaction was carried out for 90 hours under the same condition as in Example 2 except that the concentration of the N-succinyl-DL-tert-leucine solution was made 1% by weight and that 0.1 ml of a 9.6 mg/ml solution of N-succinylamino acid racemase prepared in the above (1) was previously added to the reaction solution. After completion of the reaction, the sample was collected therefrom and subjected to an HPLC measurement under the same condition as in Example 2 to calculate the yield of L-tert-leucine whereupon the yield was not lower than 90% and the value being nearly equal to 100% which is the theoretically highest yield was achieved.

Example 5

Synthesis of L-tert-leucine from N-succinyl-DL-tert-leucine Using the L-succinylaminoacylase of the Present Invention and N-Succinylamino Acid Racemase (ii)

The same reaction as in Example 4 was carried out for 120 hours except that the product prepared in the above (2) was used as an N-succinylamino acid racemase. The sample was collected after 24 hours, 48 hours and 120 hours from the start of the reaction and subjected to an HPLC measurement under the same condition as in Example 2 to confirm the synthesis of L-tert-leucine from N-succinyl-DL-tert-leucine.

Figure 2:
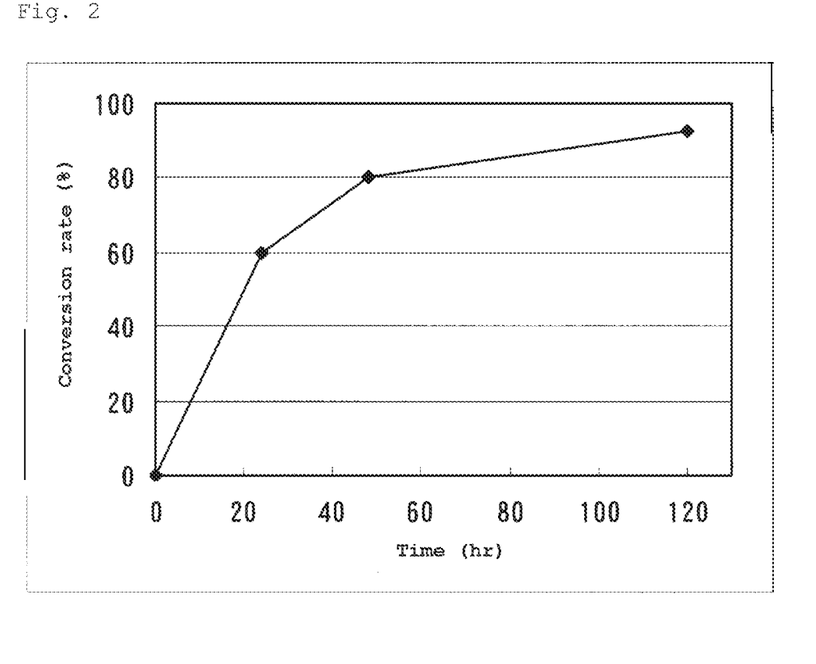
FIG. 2 shows the result of measurement of the yield of L-tert-leucine in Example 5 by means of HPLC. Time elapsed from the initiation of the reaction (hr) is shown in the abscissa while a conversion rate into L-tert-leucine (%) is shown in the ordinate.

Result of the HPLC measurement is shown in FIG. 2. As will be apparent from FIG. 2, it was possible to convert nearly all (yield of not lower than 90%) of N-succinyl-DL-tert-leucine to L-tert-leucine by the combined use of the L-succinylaminoacylase of the present invention and the N-succinylamino acid racemase.

Example 6

Comparative Experiment for Enzymatic Activity of L-succinylaminoacylase of the Present Invention with that of L-succinylaminoacylase Disclosed in Patent Document 3 (i)

The N-succinyl-DL-tert-leucine synthesized in the above (1) was dissolved in distilled water and its pH was adjusted using 0.1N sodium hydroxide (manufactured by Nacalai tesque) to prepare a 5% by weight solution of N-succinyl-DL-tert-leucine (pH 7 to 8). To 10 ml of this solution were added 0.5 mM (final concentration) of $CoCl_2$ and 0.1 ml of the N-succinylamino acid racemase in the above (2) prepared in 10 mg/ml. To the resulting solution was added 0.1 ml of the L-succinylaminoacylase disclosed in Example 1 of Patent Document 3 made into 2.5 mg/ml or a solution of the L-succinylaminoacylase of the present invention prepared in the above Example 1 and made into 2.5 mg/ml. The prepared reaction solution was kept at 50° C. for 144 hours with stirring. The sample was collected after 24 hours, 48 hours, 72 hours and 144 hours from the start of the reaction and subjected to an HPLC measurement to confirm the peaks of succinyl-form compound and free-form compound whereby the synthesis of L-tert-leucine from N-succinyl-DL-tert-leucine was confirmed.

Figure 3:
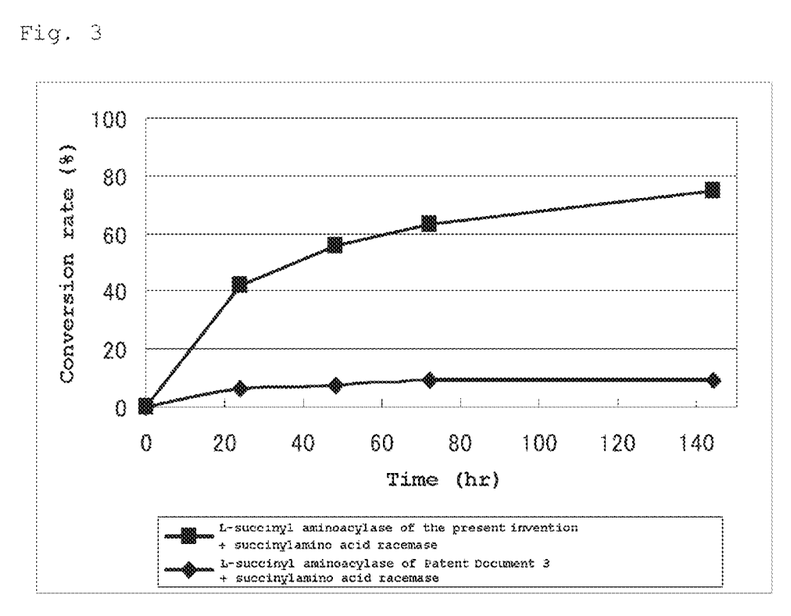
FIG. 3 shows the result of measurement of the yield of L-tert-leucine in Example 6 by means of HPLC. Time elapsed from the initiation of the reaction (hr) is shown in the abscissa while a conversion rate into L-tert-leucine (%) is shown in the ordinate.

Result of the HPLC measurement is shown in FIG. 3. As will be apparent from FIG. 3, the L-succinylaminoacylase of the present invention showed a significantly high conversion rate from N-succinyl-DL-tert-leucine to L-tert-leucine whereby the reactivity was significantly enhanced as compared with the L-succinylaminoacylase disclosed in Patent Document 3. It is apparent from this result that the L-succinylaminoacylase of the present invention is able to efficiently utilize N-succinyl-L-tert-leucine as a substrate.

Example 7

Comparative Experiment for Enzymatic Activity of L-succinylaminoacylase of the Present Invention with that of L-succinylaminoacylase Disclosed in Patent Document 3 (ii)

Each of N-succinyl-DL-4-bromophenylalanine, N-succinyl-DL-biphenylalanine, N-succinyl-DL-3,4-dichlorophenylalanine, N-succinyl-DL-cyclohexylglycine, and N-succinyl-DL-tert-leucine synthesized in the above (3) was used to prepare an amino acid solution of 10% by weight (pH 7.5). Mixed solution of 0.25 ml of 0.1M HEPES-NaOH buffer (pH 7.5), 0.025 ml of 0.1M cobalt acetate solution, 0.5 ml of each amino acid solution and 4.2 ml of distilled water was prepared. To the resulting solution was added 0.025 ml of a solution of the L-succinylaminoacylase disclosed in Example 1 of Patent Document 3 made into 5 mg/ml or a solution of the L-succinylaminoacylase of the present invention prepared in the above Example 1 made into 5 mg/ml. The resulting reaction solution was subjected to a reaction for 4 hours with stirring at 50° C. After completion of the reaction, a sample was collected therefrom and subjected to an HPLC measurement under the same condition as in Example 2 to calculate the conversion rate into each of the L-amino acids corresponding to N-succinyl-DL-4-bromophenylalanine, N-succinyl-DL-biphenylalanine, N-succinyl-DL-3,4-dichlorophenylalanine, N-succinyl-DL-cyclohexylglycine, and N-succinyl-DL-tert-leucine.

Result is shown in Table 2. As will be apparent from Table 2, the L-succinylaminoacylase of the present invention is able to synthesize each of the corresponding L-amino acids in a high conversion rate from any of N-succinyl-DL-4-bromophenylalanine, N-succinyl-DL-biphenylalanine, N-succinyl-DL-3,4-dichlorophenylalanine, N-succinyl-DL-cyclohexylglycine, and N-succinyl-DL-tert-leucine. On the contrary, although the L-succinylaminoacylase disclosed in Patent Document 3 is able to synthesize each of the corresponding L-amino acids from N-succinyl-DL-4-bromophenylalanine, and N-succinyl-DL-3,4-dichlorophenylalanine in a high conversion rate, said conversion rate is considerably low for N-succinyl-DL-biphenylalanine, N-succinyl-DL-cyclohexylglycine, and N-succinyl-DL-tert-leucine. It is apparent from the result that the L-succinylaminoacylase of the present invention is able to efficiently utilize the unnatural amino acid which is unable to be efficiently utilized as a substrate by the L-succinylaminoacylase disclosed in Patent Document 3.

TABLE 2

| Substrate | Conversion rate by L-succinyl aminoacylase of Patent Document 3 (%) | Conversion rate by L-succinyl aminoacylase of the present invention (%) |
|---|---|---|
| N-succinyl-DL-4-bromophenylalanine | 97.1 | 97.5 |
| N-succinyl-DL-biphenylalanine | 8.8 | 74.1 |
| N-succinyl-DL-dichlorophenylalanine | 82.0 | 83.3 |
| N-succinyl-DL-cyclohexylglycine | 53.6 | 97.3 |
| N-succinyl-DL-tert-leucine | 0.1 | 45.7 |

Industrial Applicability

The L-succinylaminoacylase of the present invention is able to efficiently produce a natural amino acid and a sterically bulky unnatural amino acid such as L-tert-leucine, L-biphenylalanine, L-cyclohexylglycine, L-dichlorophenylalanine or L-bromophenylalanine. Therefore, the L-succinylaminoacylase of the present invention can be widely utilized for the production of L-amino acids which are useful as intermediates or materials for pharmaceuticals, agricultural chemicals, foods, etc.

Sequence Listing Free Text

Sequence ID Nos:4, 5, 7 and 8 are the sequences of the primers used in the Examples.

Sequence ID No:6 is the sequence of the DNA coding for NAAAR which has been designed to be efficiently expressed in *Escherichia coli* K-12 strain.

The invention claimed is:

1. An isolated protein comprising the amino acid sequence of SEQ ID NO: 2.

2. A recombinant vector comprising an isolated polynucleotide, wherein the isolated polynucleotide comprises:
   (a) the nucleotide sequence of SEQ ID NO: 1; or
   (b) a nucleotide sequence encoding the amino acid sequence of SEQ ID NO: 2.

3. A process for producing an isolated protein comprising: transforming an isolated host cell with the recombinant vector of claim 2 to prepare a transformant; and culturing the transformant to produce a protein comprising the amino acid sequence of SEQ ID NO: 2; and isolating the protein.

4. A process for producing an L-amino acid, comprising contacting the isolated protein of claim 1 with a mixture of N-succinyl-DL-amino acid to hydrolyze N-succinyl-L-amino acid.

5. The process according to claim 4, further comprising racemizing N-succinyl-D-amino acid using N-succinylamino acid racemase to produce N-succinyl-L-amino acid.

6. The process according to claim 5, wherein the step of hydrolyzing N-succinyl-L-amino acid in a mixture of N-succinyl-DL-amino acid and the step of racemizing N-succinyl-D-amino acid using N-succinylamino acid racemase to produce N-succinyl-L-amino acid are conducted simultaneously.

7. The process according to any one of claims 4 to 6, wherein the N-succinyl-DL-amino acid is N-succinyl-DL-tert-leucine, N-succinyl-DL-biphenylalanine, N-succinyl-DL-cyclohexylglycine, N-succinyl-DL-dichlorophenylalanine or N-succinyl-DL-bromophenylalanine.

8. The process according to claim 7, wherein the N-succinyl-DL-amino acid is N-succinyl-DL-tert-leucine, N-succinyl-DL-biphenylalanine, or N-succinyl-DL-cyclohexylglycine.

9. A solution comprising the isolated protein of claim 1, wherein the isolated protein specifically hydrolyzes N-succinyl-L-amino acid in a mixture of N-succinyl-DL-amino acid.

* * * * *

SEQUENCE LISTING

<160> NUMBER OF SEQ ID NOS: 8

<210> SEQ ID NO 1
<211> LENGTH: 1161
<212> TYPE: DNA
<213> ORGANISM: Geobacillus stearothermophilus
<220> FEATURE:
<221> NAME/KEY: CDS
<222> LOCATION: (1)..(1161)

<400> SEQUENCE: 1

```
atg aaa gaa att att cag cag atg aaa gcg gag cta tgg agt att ttt      48
Met Lys Glu Ile Ile Gln Gln Met Lys Ala Glu Leu Trp Ser Ile Phe
1               5                   10                  15 gac tat ctt cat cgt cat ccg gaa att agt tgg gaa gaa tgg gga aca      96
Asp Tyr Leu His Arg His Pro Glu Ile Ser Trp Glu Glu Trp Gly Thr
            20                  25                  30
```

```
                                          -continued acg gaa ttt gtt cgc cgg gag ttg gaa cgc gaa ggg tat cgg gtg tgg    144
Thr Glu Phe Val Arg Arg Glu Leu Glu Arg Glu Gly Tyr Arg Val Trp
         35                  40                  45 acg ttt gcc gat tgt ccg ggc gtg gtg gca gaa atc ggc gat ggg ccg    192
Thr Phe Ala Asp Cys Pro Gly Val Val Ala Glu Ile Gly Asp Gly Pro
 50                  55                  60 ttt atg gtt ggc gtg cgc agt gat atg gat gct ctt tgg caa gag gta    240
Phe Met Val Gly Val Arg Ser Asp Met Asp Ala Leu Trp Gln Glu Val
65                  70                  75                  80 aac ggt gtt tgg cag ccg aat cat gcg tgc gga cat gac gcc cat atg    288
Asn Gly Val Trp Gln Pro Asn His Ala Cys Gly His Asp Ala His Met
                 85                  90                  95 acg atc gtg ttg ggg gtg gcg aag ctg ctt cgc cgc atc ggc tat gag    336
Thr Ile Val Leu Gly Val Ala Lys Leu Leu Arg Arg Ile Gly Tyr Glu
            100                 105                 110 ccg ccg ggg acg ctt cgg ttt ttg ttc cag cca gct gaa gag aaa ggt    384
Pro Pro Gly Thr Leu Arg Phe Leu Phe Gln Pro Ala Glu Glu Lys Gly
        115                 120                 125 aca ggg gcg ttg aag ctg att gaa aag gga gcg gtc gat gga atg tcg    432
Thr Gly Ala Leu Lys Leu Ile Glu Lys Gly Ala Val Asp Gly Met Ser
    130                 135                 140 ttt ttg tac ggc gtt cat ttg cga ccg gtt caa gaa gtc aag agc ggg    480
Phe Leu Tyr Gly Val His Leu Arg Pro Val Gln Glu Val Lys Ser Gly
145                 150                 155                 160 tat gcg aca ccg gca atc att cac ggg gca gcc caa tgc atc gaa ggg    528
Tyr Ala Thr Pro Ala Ile Ile His Gly Ala Ala Gln Cys Ile Glu Gly
                165                 170                 175 cgg att cgc ggt atg gca gcg cac gcg gcg cgg cct cat tta ggt gtg    576
Arg Ile Arg Gly Met Ala Ala His Ala Ala Arg Pro His Leu Gly Val
            180                 185                 190 aat gtc att gaa gtc ggc agt gcc atc gtg cag gag ctc ggc aaa atc    624
Asn Val Ile Glu Val Gly Ser Ala Ile Val Gln Glu Leu Gly Lys Ile
        195                 200                 205 cat gtt gac ccg caa gta cca gca acg atc aaa atg acg agg ttt cat    672
His Val Asp Pro Gln Val Pro Ala Thr Ile Lys Met Thr Arg Phe His
    210                 215                 220 gcg ggg gaa aaa gat gtg aac acg att cca gat tac gct gag ttc tcc    720
Ala Gly Glu Lys Asp Val Asn Thr Ile Pro Asp Tyr Ala Glu Phe Ser
225                 230                 235                 240 ttg gac ttg cga gcg cag acg aac gag gcg atg gag cag ctc gtc gaa    768
Leu Asp Leu Arg Ala Gln Thr Asn Glu Ala Met Glu Gln Leu Val Glu
                245                 250                 255 agg ttg cgc cgt gtg gtc aac gga gtc gct gct att tac ggg gct gag    816
Arg Leu Arg Arg Val Val Asn Gly Val Ala Ala Ile Tyr Gly Ala Glu
            260                 265                 270 att gag ctt gat gaa cgg acg cga atc gtc gcc gcc aac cct gac ttg    864
Ile Glu Leu Asp Glu Arg Thr Arg Ile Val Ala Ala Asn Pro Asp Leu
        275                 280                 285 gat gcc aag agg ctc atg gaa gag gcg atc atc gct gtt cta ggg gag    912
Asp Ala Lys Arg Leu Met Glu Glu Ala Ile Ile Ala Val Leu Gly Glu
    290                 295                 300 gag aaa tgt att ccg cca gtc atc aca tcc ggc ggg gaa gat ttc cat    960
Glu Lys Cys Ile Pro Pro Val Ile Thr Ser Gly Gly Glu Asp Phe His
305                 310                 315                 320 ttt tac gca ttt aaa aaa ccg gag ttg aaa acg acg atg ctc ggg tta   1008
Phe Tyr Ala Phe Lys Lys Pro Glu Leu Lys Thr Thr Met Leu Gly Leu
                325                 330                 335 ggc tgc gac tta cgc ccg ggg ctt cac cac ccg cag atg aca ttc caa   1056
Gly Cys Asp Leu Arg Pro Gly Leu His His Pro Gln Met Thr Phe Gln
            340                 345                 350
```

```
cgt gac gat tta ctt tcc ggc att gag att ttg gcg cgg acg gtc atc    1104
Arg Asp Asp Leu Leu Ser Gly Ile Glu Ile Leu Ala Arg Thr Val Ile
        355                 360                 365 aat acg ttt gcg cta caa gga gag aaa gaa cgt gtc tct atc gct gca    1152
Asn Thr Phe Ala Leu Gln Gly Glu Lys Glu Arg Val Ser Ile Ala Ala
370                 375                 380 aat cat tga                                                        1161
Asn His
385

<210> SEQ ID NO 2
<211> LENGTH: 386
<212> TYPE: PRT
<213> ORGANISM: Geobacillus stearothermophilus

<400> SEQUENCE: 2

Met Lys Glu Ile Ile Gln Gln Met Lys Ala Glu Leu Trp Ser Ile Phe
1               5                   10                  15

Asp Tyr Leu His Arg His Pro Glu Ile Ser Trp Glu Glu Trp Gly Thr
            20                  25                  30

Thr Glu Phe Val Arg Arg Glu Leu Glu Arg Glu Gly Tyr Arg Val Trp
        35                  40                  45

Thr Phe Ala Asp Cys Pro Gly Val Val Ala Glu Ile Gly Asp Gly Pro
    50                  55                  60

Phe Met Val Gly Val Arg Ser Asp Met Asp Ala Leu Trp Gln Glu Val
65                  70                  75                  80

Asn Gly Val Trp Gln Pro Asn His Ala Cys Gly His Asp Ala His Met
                85                  90                  95

Thr Ile Val Leu Gly Val Ala Lys Leu Leu Arg Arg Ile Gly Tyr Glu
            100                 105                 110

Pro Pro Gly Thr Leu Arg Phe Leu Phe Gln Pro Ala Glu Glu Lys Gly
        115                 120                 125

Thr Gly Ala Leu Lys Leu Ile Glu Lys Gly Ala Val Asp Gly Met Ser
    130                 135                 140

Phe Leu Tyr Gly Val His Leu Arg Pro Val Gln Glu Val Lys Ser Gly
145                 150                 155                 160

Tyr Ala Thr Pro Ala Ile Ile His Gly Ala Ala Gln Cys Ile Glu Gly
                165                 170                 175

Arg Ile Arg Gly Met Ala Ala His Ala Ala Arg Pro His Leu Gly Val
            180                 185                 190

Asn Val Ile Glu Val Gly Ser Ala Ile Val Gln Glu Leu Gly Lys Ile
        195                 200                 205

His Val Asp Pro Gln Val Pro Ala Thr Ile Lys Met Thr Arg Phe His
    210                 215                 220

Ala Gly Glu Lys Asp Val Asn Thr Ile Pro Asp Tyr Ala Glu Phe Ser
225                 230                 235                 240

Leu Asp Leu Arg Ala Gln Thr Asn Glu Ala Met Glu Gln Leu Val Glu
                245                 250                 255

Arg Leu Arg Arg Val Val Asn Gly Val Ala Ala Ile Tyr Gly Ala Glu
            260                 265                 270

Ile Glu Leu Asp Glu Arg Thr Arg Ile Val Ala Ala Asn Pro Asp Leu
        275                 280                 285

Asp Ala Lys Arg Leu Met Glu Glu Ala Ile Ile Ala Val Leu Gly Glu
    290                 295                 300

Glu Lys Cys Ile Pro Pro Val Ile Thr Ser Gly Gly Glu Asp Phe His
305                 310                 315                 320
```

```
Phe Tyr Ala Phe Lys Lys Pro Glu Leu Lys Thr Thr Met Leu Gly Leu
            325                 330                 335

Gly Cys Asp Leu Arg Pro Gly Leu His His Pro Gln Met Thr Phe Gln
        340                 345                 350

Arg Asp Asp Leu Leu Ser Gly Ile Glu Ile Leu Ala Arg Thr Val Ile
            355                 360                 365

Asn Thr Phe Ala Leu Gln Gly Glu Lys Glu Arg Val Ser Ile Ala Ala
    370                 375                 380

Asn His
385

<210> SEQ ID NO 3
<211> LENGTH: 1128
<212> TYPE: DNA
<213> ORGANISM: Geobacillus stearothermophilus
<220> FEATURE:
<221> NAME/KEY: CDS
<222> LOCATION: (1)..(1128)

<400> SEQUENCE: 3 atg gcg atc aac atc gag tac gtc ata ttg cgc cat tta caa atg gag     48
Met Ala Ile Asn Ile Glu Tyr Val Ile Leu Arg His Leu Gln Met Glu
 1               5                  10                  15 ttg aag gcg ccg ttt acg acg agc ttc ggc acg ttt caa agg aaa gag     96
Leu Lys Ala Pro Phe Thr Thr Ser Phe Gly Thr Phe Gln Arg Lys Glu
                20                  25                  30 ttg att tta gtg gaa gtt gtc gat cgc gac ggc gtt tcc ggc tgg ggc    144
Leu Ile Leu Val Glu Val Val Asp Arg Asp Gly Val Ser Gly Trp Gly
            35                  40                  45 gaa tcg gtc gca ttt tcc gcc ccg tgg tac agc gag gaa acg gtg aaa    192
Glu Ser Val Ala Phe Ser Ala Pro Trp Tyr Ser Glu Glu Thr Val Lys
        50                  55                  60 acg aac tgg cat atg ctc gaa gat ttc ctt gtg ccg ctt gcg ttg gct    240
Thr Asn Trp His Met Leu Glu Asp Phe Leu Val Pro Leu Ala Leu Ala
 65                  70                  75                  80 gag ccg att cac cac ccg gag gag ctg tca aag cgc ttt tct gcc atc    288
Glu Pro Ile His His Pro Glu Glu Leu Ser Lys Arg Phe Ser Ala Ile
                 85                  90                  95 cgc caa aac aac atg gcg aaa gcg gcg ctt gag ggg gcg gta tgg gat    336
Arg Gln Asn Asn Met Ala Lys Ala Ala Leu Glu Gly Ala Val Trp Asp
                100                 105                 110 ttg tac gcc aag cgg ctc ggc gtt ccg ctt tct caa gct ctc gga gga    384
Leu Tyr Ala Lys Arg Leu Gly Val Pro Leu Ser Gln Ala Leu Gly Gly
            115                 120                 125 gcg aaa aag gac att gaa gtc ggc gtc agc atc ggc atc cag ccg acg    432
Ala Lys Lys Asp Ile Glu Val Gly Val Ser Ile Gly Ile Gln Pro Thr
        130                 135                 140 gtt gcc gat ctg ctt cag gtg att gag cgg tat gtg gcg caa ggg tac    480
Val Ala Asp Leu Leu Gln Val Ile Glu Arg Tyr Val Ala Gln Gly Tyr
145                 150                 155                 160 cgg cgg atc aag gtg aaa atc aag cca agc tgg gat gtg gac gtc att    528
Arg Arg Ile Lys Val Lys Ile Lys Pro Ser Trp Asp Val Asp Val Ile
                165                 170                 175 cgt gag gtg cgg cgc gtg ttt cct gac gtg ccg ctt atg gcc gat gcc    576
Arg Glu Val Arg Arg Val Phe Pro Asp Val Pro Leu Met Ala Asp Ala
                180                 185                 190 aat tcg gcg tat acg ctt gtc gat gcg gat cgg ctg aaa gcg ctc gat    624
Asn Ser Ala Tyr Thr Leu Val Asp Ala Asp Arg Leu Lys Ala Leu Asp
            195                 200                 205
```

```
gaa ttc ggg ttg ctg atg atc gag cag ccg ctc gcc gct gac gat ctt    672
Glu Phe Gly Leu Leu Met Ile Glu Gln Pro Leu Ala Ala Asp Asp Leu
    210                 215                 220 gtc gat cac gct cgg ctg cag ccg ctt ctt cag acg ccg att tgc ctt    720
Val Asp His Ala Arg Leu Gln Pro Leu Leu Gln Thr Pro Ile Cys Leu
225                 230                 235                 240 gat gaa agc att cgt tcc tat gac gat gcg cgc aag gcg ctt gac ctt    768
Asp Glu Ser Ile Arg Ser Tyr Asp Asp Ala Arg Lys Ala Leu Asp Leu
                245                 250                 255 ggc agc tgt cgc atc atc aac atc aaa atc ggg cgc gtt ggc ggg ctt    816
Gly Ser Cys Arg Ile Ile Asn Ile Lys Ile Gly Arg Val Gly Gly Leu
            260                 265                 270 ggc gag gcg aag cgc atc cac gat ctt tgc gct gag cgc ggt gcg ccg    864
Gly Glu Ala Lys Arg Ile His Asp Leu Cys Ala Glu Arg Gly Ala Pro
        275                 280                 285 gtc tgg tgc ggg ggg atg ctg gaa gca ggc gtc ggg cgc gcc cac aac    912
Val Trp Cys Gly Gly Met Leu Glu Ala Gly Val Gly Arg Ala His Asn
    290                 295                 300 atc gcg atc acg acg ttg gaa aac ttc acc ctt ccc ggc gac acc gcc    960
Ile Ala Ile Thr Thr Leu Glu Asn Phe Thr Leu Pro Gly Asp Thr Ala
305                 310                 315                 320 gcg tcg tcg cat tat tgg gag cgg gat atc atc acg ccg gaa gtt gag   1008
Ala Ser Ser His Tyr Trp Glu Arg Asp Ile Ile Thr Pro Glu Val Glu
                325                 330                 335 gtg cac ggc ggc ttg atc cgc gtg ccg gac gct ccc ggc atc ggc tat   1056
Val His Gly Gly Leu Ile Arg Val Pro Asp Ala Pro Gly Ile Gly Tyr
            340                 345                 350 gac gtc gac cgc cgc caa gtg gag cgg tat acg cag ttt gcg aag gtg   1104
Asp Val Asp Arg Arg Gln Val Glu Arg Tyr Thr Gln Phe Ala Lys Val
        355                 360                 365 ttt cat cgt acg gcg acg gca taa                                   1128
Phe His Arg Thr Ala Thr Ala
    370                 375

<210> SEQ ID NO 4
<211> LENGTH: 32
<212> TYPE: DNA
<213> ORGANISM: Artificial
<220> FEATURE:
<223> OTHER INFORMATION: Primer

<400> SEQUENCE: 4
aaggaggtaa aatggcgatc aacatcgagt ac                                32

<210> SEQ ID NO 5
<211> LENGTH: 30
<212> TYPE: DNA
<213> ORGANISM: Artificial
<220> FEATURE:
<223> OTHER INFORMATION: Primer

<400> SEQUENCE: 5
tctagattat gccgtcgccg tacgatgaaa                                   30

<210> SEQ ID NO 6
<211> LENGTH: 1107
<212> TYPE: DNA
<213> ORGANISM: Artificial
<220> FEATURE:
<223> OTHER INFORMATION: DNA encoding NAAAR designed to be efficiently
      expressed in E. coli strain K-12.
<220> FEATURE:
<221> NAME/KEY: CDS
<222> LOCATION: (1)..(1107)
```

<400> SEQUENCE: 6

```
atg cgt att gag gcg att gaa ctg cgt cgc att cgt tta cca tat cgt      48
Met Arg Ile Glu Ala Ile Glu Leu Arg Arg Ile Arg Leu Pro Tyr Arg
1               5                   10                  15 gca ccg ttc gaa acg agc ggg tgg cgc gaa gaa gcc aat cat tcg gtg      96
Ala Pro Phe Glu Thr Ser Gly Trp Arg Glu Glu Ala Asn His Ser Val
            20                  25                  30 att gtg acc ctg cat agc gaa ggt gta gtg ggc tgg ggc gaa gct ccg     144
Ile Val Thr Leu His Ser Glu Gly Val Val Gly Trp Gly Glu Ala Pro
        35                  40                  45 gtt ggc gtg ggt ccg tgg tat aac gaa gaa acc caa tct acc gcg tgg     192
Val Gly Val Gly Pro Trp Tyr Asn Glu Glu Thr Gln Ser Thr Ala Trp
50                  55                  60 gtg atg atg cgc gaa att ctg gcc ccg atg ctg ctg ggt cgt gat ctg     240
Val Met Met Arg Glu Ile Leu Ala Pro Met Leu Leu Gly Arg Asp Leu
65                  70                  75                  80 agc cgt cca gaa gag gtg gat gcg atc ttt acc cgt gtg cgc ggc aac     288
Ser Arg Pro Glu Glu Val Asp Ala Ile Phe Thr Arg Val Arg Gly Asn
                85                  90                  95 cgc atg gca cgc gcg ggt ctt gag ttc gcc gcc tgg gat ctg ttc ggc     336
Arg Met Ala Arg Ala Gly Leu Glu Phe Ala Ala Trp Asp Leu Phe Gly
            100                 105                 110 cgc gca cag ggc acg agc ctc agc aca atg ctg ggc ggc acc cgt caa     384
Arg Ala Gln Gly Thr Ser Leu Ser Thr Met Leu Gly Gly Thr Arg Gln
        115                 120                 125 cgc gtg gaa gtt ggt gtc agt gtt ggt gtc cag gaa tcg att gag gcg     432
Arg Val Glu Val Gly Val Ser Val Gly Val Gln Glu Ser Ile Glu Ala
    130                 135                 140 ttg ctt gat gtg gtt gcg ggt tat gtc aat gcc ggt tac cag cgt gtg     480
Leu Leu Asp Val Val Ala Gly Tyr Val Asn Ala Gly Tyr Gln Arg Val
145                 150                 155                 160 aaa ctc aag att aaa ccg ggc tgg gat gtg gaa cca aca cgt gct gta     528
Lys Leu Lys Ile Lys Pro Gly Trp Asp Val Glu Pro Thr Arg Ala Val
                165                 170                 175 cgc gag cgc tgg ccg gat ctg cgc tta cag gtt gat gcg aac agc atc     576
Arg Glu Arg Trp Pro Asp Leu Arg Leu Gln Val Asp Ala Asn Ser Ile
            180                 185                 190 tac acc ctg gat cag gcc gac cag ttg gcg cgc ctg gac gaa ttt gat     624
Tyr Thr Leu Asp Gln Ala Asp Gln Leu Ala Arg Leu Asp Glu Phe Asp
        195                 200                 205 ctg tta ttg att gag cag ccg ctg gcg cat gac gac atc atc gat cac     672
Leu Leu Leu Ile Glu Gln Pro Leu Ala His Asp Asp Ile Ile Asp His
    210                 215                 220 gcc aaa ctt cag cgt ctg ctc cgc acg ccg att tgt ctg gat gaa agc     720
Ala Lys Leu Gln Arg Leu Leu Arg Thr Pro Ile Cys Leu Asp Glu Ser
225                 230                 235                 240 att gtc tcg cca gat cat gcg cgc tgg gca att gag tta ggt gcc tgc     768
Ile Val Ser Pro Asp His Ala Arg Trp Ala Ile Glu Leu Gly Ala Cys
                245                 250                 255 ggc gta atc aat atc aaa ccg tcg cgt gtt ggt ggt ttt acg gca gcg     816
Gly Val Ile Asn Ile Lys Pro Ser Arg Val Gly Gly Phe Thr Ala Ala
            260                 265                 270 cgt cgc att cac gat ctg gca cag gcc gcg ggt atc ccg gtg tgg tgc     864
Arg Arg Ile His Asp Leu Ala Gln Ala Ala Gly Ile Pro Val Trp Cys
        275                 280                 285 ggt ggc atg ctg gaa acg ggc atc ggg cgc gct gcc aac gtc ggt ctg     912
Gly Gly Met Leu Glu Thr Gly Ile Gly Arg Ala Ala Asn Val Gly Leu
    290                 295                 300
```

-continued

| | | | | | | | | | | | | | | | |
|---|---|---|---|---|---|---|---|---|---|---|---|---|---|---|---|
| gcg | agt | ctg | ccg | aac | ttt | agc | ctg | ccg | ggc | gac | atc | agc | gcg | aat | gat | 960
| Ala | Ser | Leu | Pro | Asn | Phe | Ser | Leu | Pro | Gly | Asp | Ile | Ser | Ala | Asn | Asp |
| 305 | | | | 310 | | | | | 315 | | | | | | 320 |

| cgc | tac | ttc | cac | cag | gac | att | gtg | acc | aac | ccg | ttt | acg | ctg | aac | ccg | 1008
| Arg | Tyr | Phe | His | Gln | Asp | Ile | Val | Thr | Asn | Pro | Phe | Thr | Leu | Asn | Pro |
| | | | | 325 | | | | | 330 | | | | | 335 | |

| gac | agt | aca | ctc | agc | gtg | cca | acc | ggg | cca | ggg | agt | ggg | gct | gag | gtc | 1056
| Asp | Ser | Thr | Leu | Ser | Val | Pro | Thr | Gly | Pro | Gly | Ser | Gly | Ala | Glu | Val |
| | | | 340 | | | | | 345 | | | | | 350 | | |

| gat | ctg | gaa | cgt | ctt | gcg | gca | gtt | acg | acc | gat | tat | gtc | atg | ctg | cgt | 1104
| Asp | Leu | Glu | Arg | Leu | Ala | Ala | Val | Thr | Thr | Asp | Tyr | Val | Met | Leu | Arg |
| | | 355 | | | | 360 | | | | | 365 | | | | |

| gcg | | | | | | | | | | | | | | | | 1107
| Ala | | | | | | | | | | | | | | | | |

<210> SEQ ID NO 7
<211> LENGTH: 40
<212> TYPE: DNA
<213> ORGANISM: Artificial
<220> FEATURE:
<223> OTHER INFORMATION: Primer

<400> SEQUENCE: 7
aaggaggtaa aatgaaagaa attattcagc agatgaaagc                              40

<210> SEQ ID NO 8
<211> LENGTH: 33
<212> TYPE: DNA
<213> ORGANISM: Artificial
<220> FEATURE:
<223> OTHER INFORMATION: Primer

<400> SEQUENCE: 8
tctagatcaa tgatttgcag cgatagagac acg                                     33